United States Patent [19]

Bittler et al.

[11] Patent Number: 4,457,925
[45] Date of Patent: Jul. 3, 1984

[54] ANDROSTANE DERIVATIVES, PROCESS FOR THEIR PRODUCTION, AND PHARMACEUTICAL PREPARATIONS CONTAINING THEM

[75] Inventors: Dieter Bittler; Henry Laurent; Klaus Nickisch; Rudolf Wiechert, all of Berlin, Fed. Rep. of Germany

[73] Assignee: Schering, Aktiengesellschaft, Berlin and Bergkamen, Fed. Rep. of Germany

[21] Appl. No.: 403,279

[22] Filed: Jul. 29, 1982

[30] Foreign Application Priority Data

Jul. 29, 1981 [DE] Fed. Rep. of Germany ....... 3130644

[51] Int. Cl.³ ................................................ C07J 1/00
[52] U.S. Cl. .................................. 424/243; 260/397.4; 260/239.55 R; 260/239.55 C
[58] Field of Search ....................................... 260/397.4

[56] References Cited

U.S. PATENT DOCUMENTS 4,180,570 12/1979 Wiechert et al. .......... 260/239.55 C

OTHER PUBLICATIONS

Kieslich, Bull. Soc. Chim. France, 1980, No. 1-2, II--9-II-17.

Primary Examiner—Elbert L. Roberts
Attorney, Agent, or Firm—Millen & White

[57] ABSTRACT

Androstane derivatives of Formula I

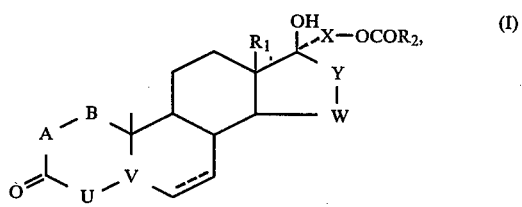

wherein
---- is a single bond or a double bond,
$R_1$ is methyl or ethyl,
$R^2$ is hydrogen or alkyl of 1-8 carbon atoms,
—X— is —$(CH_2)_n$—, —CH=CH$(CH_2)_m$—, or —C≡C—$(CH_2)_m$—
wherein n is 2 to 6 and m is 1 to 4,
—A—B— is —$CH_2$—$CH_2$—, —CH=CH—, —CCl=CH—,

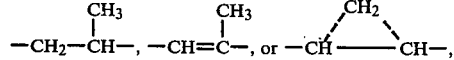

—U—V< is —$CH_2$—CH<, —CH=C<, —C(OH)=C<, or —CCl=C<, and
—W—Y— is —$CH_2$—$CH_2$—, —$CH_2$—$C(CH_3)_2$—, or

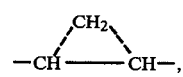

with the proviso that the compound is not 17α-(3-acetoxypropyl)-17β-hydroxy-4,6-androstadien-3-one, are pharmacologically efficacious compounds, e.g., are sebum suppressive.

44 Claims, No Drawings

ANDROSTANE DERIVATIVES, PROCESS FOR THEIR PRODUCTION, AND PHARMACEUTICAL PREPARATIONS CONTAINING THEM

The present invention relates to new androstanes having very valuable pharmacological properties.

SUMMARY OF THE INVENTION

It is an object of this invention to provide new compounds having pharmacological activity.

Upon further study of the specification and appended claims, further objects and advantages of this invention will become apparent to those skilled in the art.

These objects have been attained by providing androstane derivatives of the Formula I

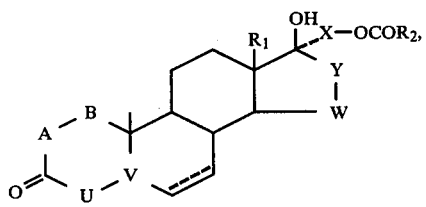

wherein
- - - is a single bond or a double bond,
$R_1$ is methyl or ethyl,
$R_2$ is hydrogen or alkyl of 1-8 carbon atoms,
—X— is —$(CH_2)_n$—, —$CH=CH(CH_2)_m$—, or —$C≡C$—$(CH_2)_m$—
wherein n is 2 to 6 and m is 1 to 4,
—A—B— is —$CH_2$—$CH_2$—, —$CH=CH$—, —$CCl=CH$—,

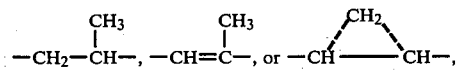

—U—V< is —$CH_2$—CH<, —$CH=C$<, —$C(OH)=C$<, or —$CCl=C$<, and
—W—Y— is —$CH_2$—$CH_2$—, —$CH_2$—$C(CH_3)_2$—, or

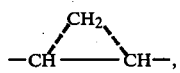

with the proviso that the compound is not 17α-(3-acetoxypropyl)-17β-hydroxy-4,6-androstadien-3-one.

DETAILED DISCUSSION

In the androstane derivatives of this invention suitable substituents $R_2$ include hydrogen or straight-chain or branched alkyl groups of 1-8 carbon atoms. Suitable such alkyl groups $R_2$ include, for example, methyl, ethyl, propyl, isopropyl, butyl, isobutyl, tertbutyl, pentyl, hexyl, octyl and the like. Preferably, $R_2$ is alkyl of 1-3, especially 2 carbon atoms.

In X, n is preferably 2-4, and especially 3; m is preferably 1 or 2, especially 1.

One particularly useful subgenus of compounds of this invention comprises compounds of Formula (Ia)

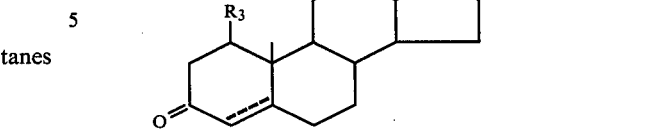

wherein
- - - and $R_2$ are as defined for Formula (I),
q is 3 or 4, and
$R_3$ is hydrogen or methyl.

The androstane derivatives of this invention (except for the compounds of Formula V which predominantly are intermediate products) are surprisingly distinguished upon local (topical) administration by a pronounced sebum-suppressive effect. Upon systemic administration, these compounds do not show any endocrinic side effects. They proved to be inactive in all tests for estrogenic, antiestrogenic, androgenic, antiandrogenic, and progestational activity. All the compounds generally are also useful, insofar as they can be used to prepare one another, e.g., using the methods described below.

The sebum-suppressive activity was determined by standard pharmacological animal studies relating to the influence of test compounds on the sebaceous glands of hamsters. The compounds of this invention inhibit lipid synthesis in the sebaceous glands of hamster ears and reduce the area sizes of the sebaceous glands and the flank organs.

For topical use, the compounds of this invention can be fully conventionally processed with the customary pharmaceutical excipients into solutions, gels, ointments, powders, or other conventional topical preparations. Suitable vehicles include, for example, water, ethanol, propanol, glycerin, methycellulose, hydroxypropylcellulose, carboxypolymethylene, etc. The sebum-suppressive agent is preferably present in a concentration of 0.05–5.0% by weight, based on the total weight of the preparation. The preparations can be utilized for the topical treatment of diseases such as acne and seborrhea. Administration is fully conventional and analogous to that for any of the many known topical agents used to treat these and similar skin diseases.

The novel androstane derivatives of this invention can be conventionally produced according to well-known methods under conditions well-known to those skilled in the art.

For example, such methods comprise, conventionally, (a) esterifying an androstane derivative of Formula II

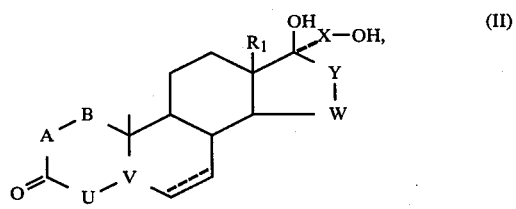

wherein

---, R₁, —X—, —A—B—, and —U—V< and —W—Y— are as defined above, with an acid of Formula III

R₂COOH    (III), or a conventional reactive derivative thereof;
or (b) hydrolytically splitting off the ketal group from an androstane derivative of Formula IV

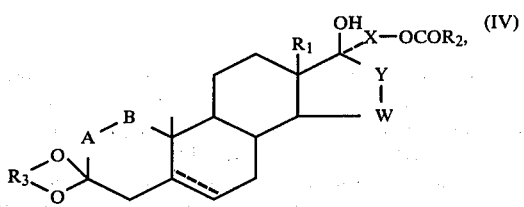

wherein
---, R₁, R₂, —X—, —A—B—, and —W—Y— are as defined above and
R₃ is a straight-chain or branched alkylene group of 2-6 carbon atoms;

(c) to prepare androstane derivatives of Formula I wherein —X— is —(CH₂)ₙ— or —CH=CH—(CH₂)ₘ—, hydrogenating an androstane derivative of Formula V

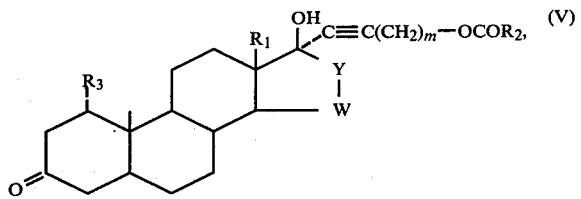

wherein
R₁, R₂, m, and —W—Y—, are as defined above and R₃ is hydrogen or methyl, to produce saturated 1α,-2α-methylene steroids of Formula I;
or (d) oxidizing the 3-hydroxy group of an androstane derivative of Formula VI

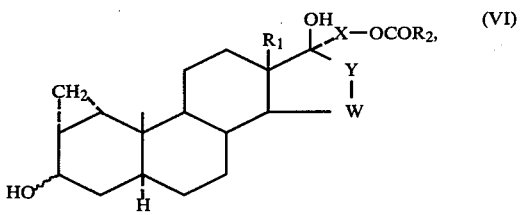

wherein R₁, R₂, —X—, and —W—Y— are as defined above with the proviso that androstane derivatives of Formula VI having a cumulative double bond are excluded, optionally with simultaneous isomerization of a resultant 5,6-double bond;
or (e) to prepare androstane derivatives of Formula I wherein —U—V< is —C(OH)=C< or —CCl=C<, reacting an androstane derivative of Formula VII

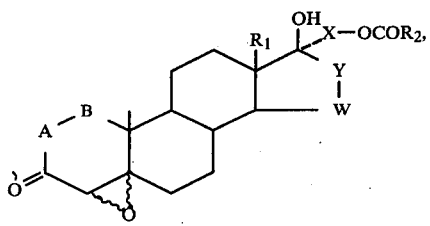

wherein —A—B—, —W—Y—, R₁, R₂, and —X— are as defined above, with a mineral acid;
or (f) to preparing androstane derivatives of Formula I with a 1,2- and/or 6,7-double bond, dehydrogenating an androstane derivative of Formula VIII

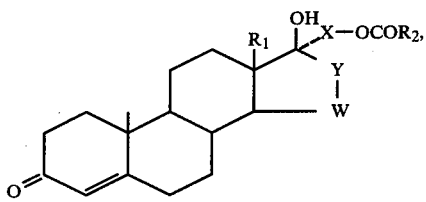

wherein R₁, R₂, —X—, and —W—Y— are as defined above.

Thus, process (a) can be conventionally performed, for example, by esterifying the androstane derivatives of Formula II with the acid chlorides or acid anhydrides in the presence of bases such as potassium carbonate, pyridine, or collidine. On the other hand, however, it is also possible to conventionally esterify these compounds with the free acids in the presence of the usual esterification catalysts such as carbonyl diimidazole, dicyclohexylcarbodiimide, or trifluoroacetic acid anhydride.

To effect process version (b), the androstane derivatives of Formula IV can be conventionally hydrolyzed, for example, with an aqueous carboxylic acid—e.g. acetic acid—or with an aqueous mineral acid in the presence of a suitable solvent, such as dioxane, tetrahydrofuran, or glycol dimethyl ether.

To effect process version (c), the androstane derivatives of Formula V can be conventionally hydrogenated, for example, in an inert solvent, such as ethanol, isopropanol, ethyl acetate, tetrahydrofuran, dioxane, benzene, toluene, etc., in the presence of a platinum or palladium catalyst, such as platinum oxide catalysts, palladium—animal charcoal catalysts, or Lindlar catalyst (L. F. Fieser and M. Fieser, Reagents for Organic Synthesis; John C. Wiley and Sons, Inc., New York etc.: 566 [1967]).

To conduct process version (d), the oxidizing agents usually employed for the oxidation of 3-hydroxy steroids can be conventionally used. Suitable oxidizing agents include, for example, chromic acid in glacial acetic acid, sodium chromate or sodium dichromate in glacial acetic acid, or, if simultaneously, a 5,6-double bond is to be isomerized to the 4,5-double bond, for example isopropylate in cyclohexanone or acetone.

To perform process version (e), the androstane derivatives of Formula VII are conventionally reacted with mineral acids. If hydrochloric acid is used for this reaction, the 4-chloro derivatives of Formula I are produced; if other acids are employed, e.g. dilute sulfuric acid or dilute perchloric acid, the 4-hydroxy compounds of Formula I are preferably formed.

In order to introduce double bonds into the androstane derivatives of Formula VIII, via process version (f), those conventional methods can be utilized, for example, which are described in C. Djerassi, Steroid Reactions, Holden Day, Inc., San Francisco: 227–266 (1963).

All of the starting compounds used in the processes of this invention are known, or can be produced in a manner known per se, e.g., as illustrated in the practical examples set forth hereinbelow.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A. A solution of 30 g of 17$\beta$-hydroxy-1$\alpha$-methyl-4-androsten-3-one in 1,250 ml of benzene is combined with 340 ml of ethylene glycol and 1.7 g of p-toluenesulfonic acid and the water formed during the reaction is distilled off azeotropically within 15 hours. After cooling of the reaction mixture, the latter is combined with 50 ml of pyridine, washed with water, dried over sodium sulfate, and concentrated under vacuum. The residue is chromatographed on silica gel. With hexane-ethyl acetate gradients (43–65% ethyl acetate), 20.7 g of 3,3-ethylenedioxy-1$\alpha$-methyl-5-androsten-17$\beta$-ol is eluted.

B. 20.7 g of 3,3-ethylenedioxy-1$\alpha$-methyl-5-androsten-17$\beta$-ol is dissolved in 470 ml of dichloromethane. The solution is combined with 20.7 g of pyridinium dichromate, stirred for 15 hours at room temperature, then washed with water, dried, and evaporated under vacuum. The residue is chromatographed on silica gel, thus eluting with hexane-ethyl acetate gradients (16–25% ethyl acetate) 14.2 g of 3,3-ethylenedioxy-1$\alpha$-methyl-5-androsten-17-one.

C. Under an argon atmosphere, 7.6 ml of propargyl alcohol dissolved in 7.6 ml of tetrahydrofuran is added dropwise, after addition of 12.6 g of potassium ethylate, to a solution of 7.6 g of 3,3-ethylenedioxy-1$\alpha$-methyl-5-androsten-17-one in 76 ml of anhydrous tetrahydrofuran within 25 minutes. The reaction mixture is then stirred for 3 hours at room temperature, combined under ice cooling with 9.8 ml of concentrated acetic acid, and exhaustively concentrated under vacuum. The residue is mixed with water and extracted with ethyl acetate; the extract is washed with water, dried, and evaporated under vacuum. The crude product is chromatographed on silica gel with an acetone-dichloromethane gradient. With 21–28% acetone, 6.0 g of 3,3-ethylenedioxy-17$\alpha$-(3-hydroxy-1-propynyl)-1$\alpha$-methyl-5-androsten-17$\beta$-ol is eluted. A sample, recrystallized from acetone-diisopropyl ether, melts at 207° C. $[\alpha]_D^{25} = -84°$ (c=0.5 in chloroform).

D. 19.5 g of 3,3-ethylenedioxy-17$\alpha$-(3-hydroxy-1-propynyl)-1$\alpha$-methyl-5-androsten-17$\beta$-ol is dissolved in a mixture of 100 ml of tetrahydrofuran and 140 ml of isopropyl alcohol and hydrogenated after adding 900 mg of palladium-calcium carbonate catalyst. After 100 minutes, hydrogen absorption is 2,225 ml at 1,018 mbar and 21° C. The catalyst is removed by vacuum-filtering over a glass filter, the filtrate is evaporated to dryness under vacuum, and the residue is chromatographed on silica gel with an acetone-dichloromethane gradient. With 32–50% acetone, after recrystallization from acetone-diisopropyl ether, 10.15 g of 3,3-ethylenedioxy-17$\alpha$-(3-hydroxypropyl)-1$\alpha$-methyl-5-androsten-17$\beta$-ol is obtained, mp 161° C. $[\alpha]_D^{25} = -36°$ (c=0.5 in chloroform).

E. 3.0 g of 3,3-ethylenedioxy-17$\alpha$-(3-hydroxypropyl)-1$\alpha$-methyl-5-androsten-17$\beta$-ol is combined with 30 ml of pyridine and 15 ml of acetic anhydride. The mixture is allowed to stand for 15 hours at room temperature whereafter the reaction product is isolated by stirring into ice water and extracting with dichloromethane. The dichloromethane solution is dried, evaporated under vacuum, and the resultant residue is dissolved in 100 ml of 90% strength acetic acid. The solution is heated on a steam bath for 30 minutes and thereafter evaporated to dryness under vacuum at elevated temperature. The residue is chromatographed on silica gel with a hexane-acetone gradient. With 33–39% acetone, after recrystallization from diethyl ether-petroleum spirits, 2.98 g of 17$\alpha$-(3-acetoxypropyl)-17$\beta$-hydroxy-1$\alpha$-methyl-4-androsten-3-one is obtained, mp 71° C. $[\alpha]_D^{25} = +70°$ (c=0.5 in chloroform). UV: $\epsilon_{243} = 13,400$ (in methanol).

EXAMPLE 2

A. A solution of 2.0 g of 3,3-ethylenedioxy-17$\alpha$-(3-hydroxypropyl)-1$\alpha$-methyl-5-androsten-17$\beta$-ol in 60 ml of 90% strength acetic acid is heated for 2 hours to 60° C. and then evaporated to dryness at 60° C. under vacuum. The residue is chromatographed with a hexane-acetone gradient on silica gel. With 55–66% acetone, after recrystallization from acetone-diisopropyl ether, 1.31 g of 17$\beta$-hydroxy-17$\alpha$-(3-hydroxypropyl)-1$\alpha$-methyl-4-androsten-3-one is obtained, mp 195° C. $[\alpha]_D^{25} = +91°$ (c=0.5 in chloroform). UV: $\epsilon_{242} = 14,800$ (in methanol).

B. 1.0 g of 17$\beta$-hydroxy-17$\alpha$-(3-hydroxypropyl)-1$\alpha$-methyl-4-androsten-3-one is dissolved in a mixture of 10 ml of pyridine and 5 ml of propionic anhydride; the solution is allowed to stand for 15 hours at room temperature. The reaction product is precipitated by stirring into ice water, vacuum-filtered, dried, and recrystallized from diethyl ether-pentane, yielding 1.07 g of 17$\beta$-hydroxy-1$\alpha$-methyl-17$\alpha$-(3-propionyloxypropyl)-4-androsten-3-one, mp 105° C. $[\alpha]_D^{25} = +73°$ (c=0.5 in chloroform). UV: $\epsilon_{243} = 14,500$ (in methanol).

EXAMPLE 3

500 mg of 17$\beta$-hydroxy-17$\alpha$-(3-hydroxypropyl)-1$\alpha$-methyl-4-androsten-3-one is dissolved in 5 ml of pyridine and 2.5 ml of butyric anhydride. The reaction takes place within 15 hours at 20° C. The product is precipitated by pouring into ice water. After one hour, the product is vacuum-filtered, dried, and recrystallized from diethyl ether-hexane, thus obtaining 403 mg of 17$\alpha$-(3-butyryloxypropyl)-17$\beta$-hydroxy-1$\alpha$-methyl-4-androsten-3-one, mp 94° C. $[\alpha]_D^{25} = +71°$ (c=0.5 in chloroform). UV: $\epsilon_{243} = 14,900$ (in methanol).

EXAMPLE 4

A. A solution of 117 g of 3,3-ethylenedioxy-5$\alpha$-pregnan-17-one in 1,170 ml of anhydrous tetrahydrofuran is combined under an argon atmosphere and with ice cooling with 194 g of potassium ethylate and then dropwise with a solution of 122 ml of propargyl alcohol in 122 ml of tetrahydrofuran within 30 minutes. The reaction mixture is stirred for 3 hours at room temperature, combined under ice cooling with 150 ml of concentrated acetic acid, and concentrated to dryness under vacuum. The residue is mixed with water and extracted with dichloromethane; the organic phase is dried and evaporated, the crude product is chromatographed on silica gel with dichloromethane-acetone gradients. With 82–100% acetone, 91.4 g of product is eluted and then recrystallized from dichloromethane-acetone, thus obtaining 84.1 g of 3,3-ethylenedioxy-17α-(3-hydroxy-1-propynyl)-5α-androstan-17β-ol, mp 219° C.

B. 60.1 g of 3,3-ethylenedioxy-17α-(3-hydroxy-1-propynyl)-5α-androstan-17β-ol is hydrogenated under the conditions of Example 1D. The crude product is triturated with acetone, filtered off, and dried. Yield: 55.0 g of 3,3-ethylenedioxy-17α-(3-hydroxypropyl)-5α-androstan-17β-ol.

C. 6.0 g of 3,3-ethylenedioxy-17α-(3-hydroxypropyl)-5α-androstan-17β-ol is made to react with 50 ml of pyridine and 25 ml of acetic anhydride within 15 hours at room temperature. The reaction product is isolated by stirring into ice water and extracting with dichloromethane and then chromatographed on silica gel. With a hexane-ethyl acetate gradient (27–42% ethyl acetate), 5.23 g is eluted, yielding after recrystallization from acetone-diisopropyl ether, 3.83 g of 17α-(3-acetoxypropyl)-3,3-ethylenedioxy-5α-androstan-17β-ol, mp 187° C. $[α]_D^{22} = -1°$ (c=0.5 in chloroform).

D. A solution of 2.0 g of 17α-(3-acetoxypropyl)-3,3-ethylenedioxy-5α-androstan-17β-ol in 24 ml of 90% strength acetic acid is heated for 30 minutes on a steam bath and then evaporated under vacuum at 60° C. The residue is chromatographed on silica gel. With 15% ethyl acetate-hexane, after recrystallization from diethyl ether-petroleum spirits, 693 mg of 17α-(3-acetoxypropyl)-17β-ol-5α-androstan-3-one is obtained, mp 96° C.

EXAMPLE 5

A. A solution of 2.5 g of 3,3-ethylenedioxy-17α-(3-hydroxypropyl)-5α-androstan-17β-ol in 30 ml of 90% strength acetic acid is heated for 30 minutes on a steam bath and then stirred into ice water. The thus-precipitated product is filtered off, washed, dried, and chromatographed on silica gel. With a mixture of 30% hexane, 60% acetone, and 10% methanol, after recrystallization from dichloromethanediisopropyl ether, 1.83 g of 17β-hydroxy-17α-(3-hydroxypropyl)-5α-androstan-3-one is obtained, mp 216° C.

B. 1.7 g of 17β-hydroxy-17α-(3-hydroxypropyl)-5α-androstan-3-one is converted according to the conditions disclosed in Example 2B into 17β-hydroxy-17α-(3-propionyloxypropyl)-5α-androstan-3-one. The crude product is recrystallized from diethyl ether-diisopropyl ether. Yield: 1.45 g, mp 100° C. $[α]_D^{22} = +12°$ (c=0.5 in chloroform).

EXAMPLE 6

Analogously to Example 3, 3.0 g of 17β-hydroxy-17α-(3-hydroxypropyl)-5α-androstan-3-one is converted into 17α-(3-butyryloxypropyl)-17β-hydroxy-5α-androstan-3-one. After recrystallizing the crude product from diethyl ether-petroleum spirits, 2.58 g is obtained, mp 72° C.

EXAMPLE 7

A. Under the conditions of Example 5A, 23.5 g of 3,3-ethylenedioxy-17α-(3-hydroxy-1-propynyl)-5α-androstan-3β-ol is used to produce 16.3 g of 17β-hydroxy-17α-(3-hydroxy-1-propynyl)-5α-androstan-3-one, mp 211° C. (from acetone-diisopropyl ether). $[α]_D^{22} = -17°$ (c=0.5 in chloroform).

B. 5.0 g of 17β-hydroxy-17α-(3-hydroxy-1-propynyl)-5α-androstan-3-one is combined with 30 ml of pyridine and 15 ml of butyric anhydride. After 15 hours, the product is isolated by precipitation with ice water and extraction with dichloromethane and recrystallized from diethyl ether-diisopropyl ether. Yield: 5.13 g of 17α-(3-butyryloxy-1-propynyl)-17β-hydroxy-5α-androstan-3-one.

C. 1.2 g of 17α-(3-butyryloxy-1-propynyl)-17β-hydroxy-5α-androstan-3-one is hydrogenated in 50 ml of benzene and 25 ml of tetrahydrofuran with 400 mg of Lindlar catalyst until one equivalent of hydrogen has been absorbed. The catalyst is filtered off, the filtrate is concentrated to dryness under vacuum, and the residue is chromatographed on silica gel. With 20% ethyl acetatehexane, after recrystallization from diethyl ether-petroleum spirits, 490 mg of 17α-(3-butyryloxy-1-propenyl)-17β-hydroxy-5α-androstan-3-one is obtained, mp 109° C.

EXAMPLE 8

A. 5.0 g of 17β-hydroxy-17α-(3-hydroxy-1-propynyl)-5α-androstan-3-one is converted analogously to Example 2B into 5.8 g of 17β-hydroxy-17α-(3-propionyloxypropynyl)-5α-androstan-3-one.

B. 5.8 g of 17β-hydroxy-17α-(3-propionyloxy-1-propynyl)-5α-androstan-3-one is hydrogenated under the conditions of Example 1D. The crude product is chromatographed on silica gel. With 22% ethyl acetate-hexane, after recrystallization from diethyl ether-petroleum spirits, 2.62 g of 17β-hydroxy-17α-(3-propionyloxy-1-propyl)-5α-androstan-3-one is produced, mp 99° C. $[α]_D^{22} = +11°$ (c=0.5 in chloroform).

EXAMPLE 9

A. 25 g of 17β-hydroxy-1-methyl-5α-androst-1-en-3-one is converted analogously to Example 1A into 3,3-ethylenedioxy-1-methylene-5α-androstan-17β-ol. In analogy to Examples 1B-C, 3,3-ethylenedioxy-17α-(3-hydroxy-1-propynyl)-1-methylene-5α-androstan-17β-ol is produced therefrom; this compound is converted, according to Example 2A, into 17β-hydroxy-17α-(3-hydroxy-1-propynyl)-1-methyl-5α-androst-1-en-3-one. Yield: 9.25 g.

B. 2.0 g of 17β-hydroxy-17α-(3-hydroxy-1-propynyl)-1-methyl-5α-androst-1-en-3-one is hydrogenated under the conditions of Example 1D. The resultant 17β-hydroxy-17α-(3-hydroxypropyl)-1-methyl-5α-androst-1-en-3-one is reacted analogously to Example 3 to 17α-(3-butyryloxypropyl)-1-methyl-5α-androst-1-en-3-one. The crude product is chromatographed on silica gel. With 20% ethyl acetate-hexane, 908 mg is obtained by elution in oily form.

EXAMPLE 10

A. A solution of 30 g of 17β-hydroxy-1α-methyl-5α-androstan-3-one in 300 ml of toluene and 90 ml of ethylene glycol is combined with 900 mg of p-toluenesulfonic acid and stirred for 6 hours with gradual removal by distillation. After cooling, the reaction solution is mixed with 3 ml of pyridine, diluted with diethyl ether, and washed with water. After evaporation, 35 g of 3,3-ethylenedioxy-1α-methyl-5α-androstan-17β-ol is obtained.

B. 35 g of 3,3-ethylenedioxy-1α-methyl-5α-androstan-17β-ol is stirred in 350 ml of dimethylformamide with 70 g of pyridinium dichromate for 17 hours at room temperature. The reaction solution is stirred into ten times the amount of ethyl acetate, then the thus-separated chromium salts are left behind by decanting, and the organic phase is washed with water. After drying and evaporation, 35 g of 3,3-ethylenedioxy-1α-methyl-5α-androstan-17-one is produced, mp 154° C.

C. A solution of 10 g of 3,3-ethylenedioxy-1α-methyl-5α-androstan-17-one in 100 ml of anhydrous tetrahydrofuran is cooled in an ice bath. Under argon, 30 g of potassium ethylate is introduced and then 20 ml of propargyl alcohol, dissolved in 40 ml of tetrahydrofuran, is added dropwise within 30 minutes. The reaction solution is stirred for 5.5 hours at room temperature, cooled in an ice bath, and combined with 23 ml of acetic acid. Thereafter the mixture is extensively concentrated under vacuum, the residue is taken up in ethyl acetate, the solution is washed with water and saturated sodium bicarbonate solution, dried, and evaporated. After recrystallization from acetone, the yield is 5.8 g of 3,3-ethylenedioxy-17α-(3-hydroxy-1-propynyl)-1α-methyl-5α-androstan-17β-ol, mp 232° C.

D. 15 g of 3,3-ethylenedioxy-17α-(3-hydroxy-1-propynyl)-1α-methyl-5α-androstan-17β-ol is stirred in 150 ml of tetrahydrofuran and 150 ml of methanol with 15 ml of 8% strength sulfuric acid for 1.5 hours at room temperature. The reaction solution is diluted with diethyl ether, washed neutral with water, dried, and evaporated. Yield: 12 g of 17β-hydroxy-17α-(3-hydroxy-1-propynyl)-1α-methyl-5α-androstan-3-one.

E. 1.0 g of 17β-hydroxy-17α-(3-hydroxy-1-propynyl)-1α-methyl-5α-androstan-3-one is allowed to stand in 2 ml of pyridine with 1 ml of propionic anhydride for 17 hours at room temperature. The reaction mixture is stirred into ice water, the thus-formed precipitate is filtered off, taken up in diethyl ether, and the solution is washed with sodium bicarbonate solution. After drying and evaporation, the residue is chromatographed, yielding 950 mg of 17β-hydroxy-1α-methyl-17α-(3-propionyloxy-1-propynyl)-5α-androstan-3-one, mp 98° C.

F. 750 mg of 17β-hydroxy-1α-methyl-17α-(3-propionyloxy-1-propynyl)-5α-androstan-3-one is hydrogenated under the conditions disclosed in Example 12A until two equivalents of hydrogen have been absorbed. The reaction product is chromatographed on silica gel, thus obtaining 673 mg of 17β-hydroxy-1α-methyl-17α-(3-propionyloxypropyl)-5α-androstan-3-one as an oil.

EXAMPLE 11

A. 2.0 g of 17β-hydroxy-17α-(3-hydroxy-1-propynyl)-1α-methyl-5α-androstan-3-one is hydrogenated in 60 ml of benzene and 40 ml of tetrahydrofuran with 600 mg of Lindlar catalyst until one equivalent of hydrogen has been absorbed. The mixture is filtered off from the catalyst and evaporated to dryness. The residue is triturated with diisopropyl ether and vacuum-filtered, thus producing 1.75 g of 17β-hydroxy-17α-(3-hydroxy-1-propenyl)-1α-methyl-5α-androstan-3-one, mp 184° C.

B. 800 mg of 17β-hydroxy-17β-(3-hydroxy-1-propenyl)-1α-methyl-5α-androstan-3-one is reacted in 1.6 ml of pyridine and 0.8 ml of propionic anhydride as described in Example 10E and worked up. After chromatography on silica gel, 730 mg of 17β-hydroxy-1α-methyl-17α-(3-propionyloxy-1-propynyl)-5α-androstan-3-one, mp 87° C., is obtained.

EXAMPLE 12

A. 7.5 g of 3,3-ethylenedioxy-17α-(3-hydroxy-1-propynyl)-1α-methyl-5α-androstan-17β-ol is hydrogenated in 120 ml of 2-propanol and 120 ml of tetrahydrofuran with 6 g of Raney nickel catalyst until two equivalents of hydrogen have been absorbed. Then the mixture is filtered off from the catalyst and evaporated to dryness under vacuum. The residue is chromatographed on silica gel. After recrystallization from diisopropyl ether-acetone, 3.5 g of 3,3-ethylenedioxy-17α-(3-hydroxypropyl)-1α-methyl-5α-androstan-17β-ol, mp 192° C., is produced.

B. 3.3 g of 3,3-ethylenedioxy-17α-(3-hydroxypropyl)-1α-methyl-5α-androstan-17β-ol is stirred in 66 ml of methanol with 3.3 ml of 8% strength sulfuric acid for one hour at room temperature. The reaction solution is diluted with diethyl ether, washed with water, dried, and evaporated. The residue is recrystallized from diisopropyl ether-acetone. Yield: 2.3 g of 17β-hydroxy-17α-(3-hydroxypropyl)-1α-methyl-5α-androstan-3-one, mp 163° C.

C. 500 mg of 17β-hydroxy-17α-(3-hydroxypropyl)-1α-methyl-5α-androstan-3-one is allowed to stand in 2 ml of pyridine and 1 ml of propionic anhydride for 17 hours at room temperature and then worked up as described in Example 10E. Chromatography on silica gel yields 460 mg of 17β-hydroxy-1α-methyl-17α-(3-propionyloxypropyl)-5α-androstan-3-one as an oil.

EXAMPLE 13

1.0 g of 17β-hydroxy-17α-(3-hydroxypropyl)-1α-methyl-5α-androstan-3-one is allowed to stand in a mixture of 4 ml of pyridine and 1 ml of butyric anhydride for 17 hours at room temperature and then worked up as disclosed in Example 10E. After chromatography on silica gel, 860 mg of 17α-(3-butyryloxypropyl)-17β-hydroxy-1α-methyl-5α-androstan-3-one is obtained as an oil. $[\alpha]_D^{23} = +3.5°$ (c=0.5 in chloroform).

EXAMPLE 14

800 mg of 17β-hydroxy-17α-(3-hydroxypropyl)-1α-methyl-5α-androstan-3-one is allowed to stand in 1.6 ml of pyridine and 0.8 ml of caproic anhydride for 24 hours at room temperature. The reaction solution is stirred into ice water, then extracted with diethyl ether, and the ether phase is washed with sodium bicarbonate solution and water. After drying and evaporation, the residue is chromatographed on silica gel, thus obtaining 950 mg of 17α-(3-hexanoyloxypropyl)-17β-hydroxy-1α-methyl-5α-androstan-3-one as an oil. $[\alpha]_D^{23} = +3.8°$ (c=0.5 in chloroform).

EXAMPLE 15

A. 10 g of 3,3-ethylenedioxy-1α-methyl-5α-androstan-17-one is dissolved in 100 ml of absolute tetrahydrofuran. Then 20 g of zinc-copper couple is added thereto and, after introducing some iodine, 40 ml of ethyl bromoacetate is added dropwise within 30 minutes. After the reaction, which in part proceeds violently, is terminated, the reaction mixture is stirred for 30 minutes at room temperature. Subsequently, saturated ammonium chloride solution is added dropwise; the reaction solution is diluted with diethyl ether and washed with water. After drying and evaporation, the residue is chromatographed on silica gel, yielding 7.9 g of (3,3-ethylenedioxy-17β-hydroxy-1α-methyl-5α-androstan-17α-yl)acetic acid ethyl ester as an oil.

B. 7.5 g of (3,3-ethylenedioxy-17β-hydroxy-1α-methyl-5α-androstan-17α-yl)acetic acid ethyl ester is combined, in 225 ml of absolute tetrahydrofuran, under ice cooling with 2.5 g of lithium alanate in incremental portions. The mixture is stirred for 1.5 hours under cooling and then 2.5 ml of water, 2.5 ml of 15% sodium hydroxide solution, and 7.5 ml of water are added in succession to the reaction solution. The product is then vacuum-filtered from the resultant precipitate, washed with tetrahydrofuran, and evaporated to dryness under vacuum. The residue is chromatographed on silica gel, yielding 4.2 g of 3,3-ethylenedioxy-17α-(2-hydroxyethyl)-1α-methyl-5α-androstan-17β-ol. A sample recrystallized from acetone-dichloromethane melts at 229° C.

C. 4.0 g of 3,3-ethylenedioxy-17α-(2-hydroxyethyl)-1α-methyl-5α-androstan-17β-ol is stirred in 80 ml of methanol and 20 ml of tetrahydrofuran with 4 ml of 8% strength sulfuric acid for 2 hours at room temperature. The reaction mixture is diluted with diethyl ether, washed with water, dried, and evaporated. The residue thus obtained is 3.5 g of 17β-hydroxy-17α-(2-hydroxyethyl)-1α-methyl-5α-androstan-3-one, mp 192° C.

D. 1.2 g of 17β-hydroxy-17α-(2-hydroxyethyl)-1α-methyl-5α-androstan-3-one is stirred in 4.8 ml of pyridine and 1.2 ml of propionic anhydride for 6 hours at room temperature. The mixture is worked up as described in Example 10E. After chromatography on silica gel, 1.26 g of 17β-hydroxy-1α-methyl-17α-(2-propionyloxyethyl)-5α-androstan-3-one, mp 124° C., is obtained.

EXAMPLE 16

A. 1.5 g of lithium is combined in 50 ml of absolute tetrahydrofuran with 10 ml of 1-chloro-4-(1-ethoxyethoxy)butane under argon. With ice cooling, 5.0 g of 3,3-ethylenedioxy-1α-methyl-5α-androstan-17-one is added thereto, and then the mixture is stirred for 3 hours at room temperature. The reaction solution is poured off from the unreacted lithium and stirred into ice water. The thus-precipitated compound is extracted with diethyl ether. After drying and evaporation, the residue is chromatographed on silica gel, thus obtaining 2.4 g of 17α-[4-(1-ethoxyethoxy)butyl]-3,3-ethylenedioxy-1α-methyl-5α-androstan-17β-ol as an oil.

B. 2.4 g of 17α-[4-(1-ethoxyethoxy)butyl]-3,3-ethylenedioxy-1α-methyl-5α-androstan-17β-ol is stirred in 24 ml of methanol with 2.4 ml of 8% strength sulfuric acid for one hour at room temperature, then diluted with diethyl ether, washed with water, dried, and evaporated. The residue is chromatographed on silica gel. By recrystallization from diisopropyl ether, 1.3 g of 17β-hydroxy-17α-(4-hydroxybutyl)-1α-methyl-5α-androstan-3-one is obtained, mp 131° C.

C. 1.1 g of 17β-hydroxy-17α-(4-hydroxybutyl)-1α-methyl-5α-androstan-3-one is allowed to stand in 2.2 ml of pyridine and 1.1 ml of propionic anhydride for 4.5 hours at room temperature and then worked up as described in Example 10E. Chromatography on silica gel yields 1.2 g of 17β-hydroxy-1α-methyl-17α-(4-propionyloxybutyl)-5α-androstan-3-one as an oil. $[\alpha]_D^{23} = +1.1°$ (c=0.5 in chloroform).

EXAMPLE 17

A. A solution of 7.0 g of 3,3-ethylenedioxy-1α-methyl-5α-androstan-17-one in 70 ml of absolute tetrahydrofuran is combined with 4.42 g of 55% strength sodium hydride-oil suspension as well as with 5.1 ml of methyl iodide and heated to boiling for 24 hours. After cooling, the mixture is diluted with diethyl ether, washed with water, dried, and evaporated, yielding 9.0 g of 3,3-ethylenedioxy-1α,16,16-trimethyl-5α-androstan-17-one. A sample triturated with 70% aqueous methanol melts at 125° C.

B. Under argon, 50 ml of absolute, ice-cooled tetrahydrofuran is combined with 52 ml of a 1.4-molar butyllithium solution in hexane. Thereafter, 2.3 ml of distilled propargyl alcohol, dissolved in 10 ml of absolute tetrahydrofuran, is added gradually dropwise to the reaction mixture. Subsequently, 3.0 g of 3,3-ethylenedioxy-1α-methyl-5α-androstan-17-one, dissolved in 30 ml of absolute tetrahydrofuran, is added thereto. The mixture is stirred for 3 hours under ice cooling and for 17 hours at room temperature. The reaction solution is stirred into ice water, extracted with dichloromethane, washed with water, dried, and evaporated. The residue is chromatographed on silica gel. Yield: 1.65 g of 3,3-ethylenedioxy-17α-(3-hydroxy-1-propynyl)-1α,16,16-trimethyl-5α-androstan-17β-ol.

C. 1.6 g of 3,3-ethylenedioxy-17α-(3-hydroxy-1-propynyl)-1α,16,16-trimethyl-5α-androstan-17β-ol is stirred in 16 ml of methanol with 1.6 ml of 8% strength sulfuric acid for one hour at room temperature. The reaction solution is diluted with diethyl ether, washed with water, dried, and evaporated, thus obtaining 1.4 g of 17β-hydroxy-17α-(3-hydroxy-1-propynyl)-1α,16,16-trimethyl-5α-androstan-3-one.

D. 1.4 g of 17β-hydroxy-17α-(3-hydroxy-1-propynyl)-1α,16,16-trimethyl-5α-androstan-3-one is hydrogenated in 10 ml of tetrahydrofuran and 10 ml of 2-propanol in the presence of 200 mg of 10% palladium-calcium carbonate catalyst until two equivalents of hydrogen have been absorbed. The catalyst is filtered off and the filtrate evaporated to dryness under vacuum. The residue is chromatographed on silica gel, thus obtaining 1.2 g of 17β-hydroxy-17α-(3-hydroxypropyl)-1α,16,16-trimethyl-5α-androstan-3-one as an oil.

E. 1.1 g of 17β-hydroxy-17α-(3-hydroxypropyl)-1α,16,16-trimethyl-5α-androstan-3-one is allowed to stand in 2.2 ml of pyridine and 1.1 ml of propionic anhydride for 4.5 hours at room temperature and then worked up as described in Example 10E. After chromatography on silica gel, 1.15 g of 17β-hydroxy-1α,16α,16β-trimethyl-17α-(3-pripionyloxypropyl)-5α-androstan-3-one is obtained as an oil.

EXAMPLE 18

A. A solution of 8.0 g of 17β-hydroxy-1α,2α-methylene-5α-androstan-3-one in 40 ml of tetrahydrofuran is combined with 8 ml of 3,4-dihydro-2H-pyran and 3 drops of phosphorus oxychloride and stirred at room temperature for 30 minutes. Subsequently the mixture is diluted with diethyl ether, washed with sodium bicarbonate solution and water, dried, and evaporated, yielding 9.0 g of 1α,2α-methylene-17β-(tetrahydropyran-2-yloxy)-5α-androstan-3-one.

B. 9.0 g of 1α,2α-methylene-17β-(tetrahydropyran-2-yloxy)-5α-androstan-3-one is stirred in 90 ml of tetrahydrofuran with 10 g of lithium tri-tert-butoxyalanate for 2.5 hours at room temperature. The reaction solution is diluted with diethyl ether, washed with 2N sulfuric acid and water, dried, and evaporated, yielding as a residue 9.0 g of 1α,2α-methylene-17β-(tetrahydropyran-2-yloxy)-5α-androstan-3-ol.

C. 9.0 g of 1α,2α-methylene-17β-(tetrahydropyran-2-yloxy)-5α-androstan-3-ol is allowed to stand in 20 ml of pyridine and 10 ml of acetic anhydride for 20 hours at room temperature. The solution is stirred into ice water, the resultant precipitate is filtered off, taken up in diethyl ether, washed with water, and dried. After evaporation, 11 g of 3-acetoxy-1α,2α-methylene-17β-(tetrahydropyran-2-yloxy)-5α-androstane is obtained.

D. A solution of 11 g of 3-acetoxy-1α,2α-methylene-17β-(tetrahydropyran-2-yloxy)-5α-androstane in 55 ml of tetrahydrofuran and 55 ml of methanol is combined with 11 ml of 8% strength sulfuric acid and stirred for 3 hours at room temperature. The reaction solution is diluted with diethyl ether, washed with water, dried, and evaporated. The residue is chromatographed on silica gel, yielding 7.0 g of 3-acetoxy-1α,2α-methylene-5α-androstan-17β-ol.

E. A solution of 6.8 g of 3-acetoxy-1α,2α-methylene-5α-androstan-17β-ol in 68 ml of dichloromethane is combined with 10.2 g of pyridinium chlorochromate and stirred for one hour at room temperature, then diluted with diethyl ether, washed with water, and dried. Evaporation yields 7.0 g of 3-acetoxy-1α,2α-methylene-5α-androstan-17-one.

F. 7.0 g of 3-acetoxy-1α,2α-methylene-5α-androstan-17-one is dissolved in 70 ml of absolute tetrahydrofuran; the solution is cooled in an ice bath and combined under argon with 17 g of potassium ethylate. Then 10.5 ml of distilled propargyl alcohol, dissolved in 10.5 ml of absolute tetrahydrofuran, is added dropwise to the reaction mixture, whereafter the latter is stirred for 3 hours at room temperature. The mixture is worked up as described in Example 1C and the residue is triturated with diisopropyl ether, thus producing 7.3 of 17α-(3-hydroxy-1-propynyl)-1α,2α-methylene-5α-androstane-3,17β-diol, mp 136° C.

G. 4.0 g of 17α-(3-hydroxy-1-propynyl)-1α,2α-methylene-5α-androstane-3,17β-diol is hydrogenated in 40 ml of tetrahydrofuran and 60 ml of 2-propanol with 400 mg of 10% palladium-calcium carbonate catalyst until two equivalents of hydrogen have been absorbed. The catalyst is filtered off, and the filtrate is evaporated to dryness under vacuum, yielding 4.0 g of 17α-(3-hydroxypropyl)-1α,2α-methylene-5α-androstane-3,17β-diol.

H. 2.0 g of 17α-(3-hydroxypropyl)-1α,2α-methylene-5α-androstane-3,17β-diol is stirred in 10 ml of dimethylformamide with 2 ml of propionic anhydride in the presence of 1.2 of lead(II) acetate for 24 hours at room temperature. The reaction solution is stirred into ice water, the resultant precipitate is filtered off and taken up in diethyl ether. The solution is washed with sodium bicarbonate solution and water, dried, and evaporated. The residue is chromatographed on silica gel, yielding 970 mg of 1α,2α-methylene-17α-(3-propionyloxypropyl)-5α-androstane-3,17β-diol.

I. 970 mg of 1α,2α-methylene-17α-(3-propionyloxypropyl)-5α-androstane-3,17β-diol is stirred in 12.5 ml of dimethylformamide with 2.91 g of pyridinium dichromate for 2 hours at room temperature. The reaction solution is stirred into ten times the amount of ethyl acetate; then the mixture is removed by decanting from the precipitated chromium salts, and the organic phase is washed with water. After drying and evaporation, the residue is chromatographed on silica gel. Recrystallization from diisopropyl ether-acetone yields 560 mg of 17β-hydroxy-1α,2α-methylene-17α-(3-propionyloxypropyl)-5α-androstan-3-one, mp 210° C.

EXAMPLE 19

A. 15 g of 2-chloro-17β-hydroxy-5α-androst-1-en-3-one is heated under reflux with the use of a water trap in 300 ml of benzene and 45 ml of ethylene glycol with 750 mg of p-toluenesulfonic acid for 2.5 hours. After cooling, the solution is combined with 2 ml of pyridine, diluted with diethyl ether, washed with water, dried, and evaporated. Yield: 17.2 g of 2-chloro-3,3-ethylenedioxy-5α-androst-1-en-17β-ol. A sample triturated with diisopropyl ether melts at 191° C.

B. 5.0 g of 2-chloro-3,3-ethylenedioxy-5α-androst-1-en-17β-ol is stirred in 50 ml of dimethylformamide with 10 g of pyidinium dichromate for 17 hours at room temperature and then worked up as described in Example 10B. After evaporation, 5 g of 2-chloro-3,3-ethylenedioxy-5α-androst-1-en-17-one is obtained.

C. A solution of 4.5 g of 2-chloro-3,3-ethylenedioxy-5α-androst-1-en-17-one in 45 ml of absolute tetrahydrofuran is cooled in an ice bath and combined under an argon atmosphere with 10.8 g of potassium ethylate. A solution of 6.75 ml of distilled propargyl alcohol in 13.5 ml of tetrahydrofuran is added dropwise thereto and then the mixture is stirred for 2 hours at room temperature. The reaction solution is diluted with dichloromethane, washed with dilute sulfuric acid and water, and dried. The residue obtained after evaporation is chromatographed on silica gel, yielding 3.75 g of 2-chloro-3,3-ethylenedioxy-17α-(3-hydroxy-1-propynyl)-5α-androst-1-en-17β-ol.

D. 3.75 g of 2-chloro-3,3-ethylenedioxy-17α-(3-hydroxy-1-propynyl)-5α-androst-1-en-17β-ol is hydrogenated in 20 ml of tetrahydrofuran and 20 ml of 2-propanol with 500 mg of 10% palladium-calcium carbonate catalyst until two equivalents of hydrogen have been absorbed. Then the product is filtered off from the catalyst and evaporated to dryness under vacuum. The residue is chromatographed on silica gel, thus obtaining 450 mg of 2-chloro-3,3-ethylenedioxy-17α-(3-hydroxypropyl)-5α-androst-1-en-17β-ol.

E. 440 mg of 2-chloro-3,3-ethylenedioxy-17α-(3-hydroxypropyl)-5α-androst-1-en-17β-ol is dissolved in 4.4 ml of tetrahydrofuran and 4.4 ml of methanol. The solution is stirred, after adding 0.88 ml of 8% strength sulfuric acid, for 5 hours at room temperature, diluted with diethyl ether, washed with water, dried, and evaporated. Yield: 415 mg of 2-chloro-17β-hydroxy-17α-(3-hydroxypropyl)-5α-androst-1-en-3-one.

F. 415 mg of 2-chloro-17β-hydroxy-17α-(3-hydroxypropyl)-5α-androst-1-en-3-one is allowed to stand at room temperature for 16 hours in 1.6 ml of pyridine and 0.8 ml of propionic anhydride and then worked up as described in Example 10E. The residue is chromographed on silica gel, yielding 370 mg of 2-chloro-17β-hydroxy-17α-(3-propionyloxypropyl)-5α-androst-1-en-3-one as an oil. $[\alpha]_D^{23} = +15°$ (c=0.5 in chloroform).

EXAMPLE 20

2.0 g of 17β-hydroxy-17α-(3-hydroxypropyl)-4-androsten-3-one is dissolved in 7 ml of formic acid. The solution is combined under ice cooling with 4 ml of acetic anhydride and stirred for 1.5 hours at 5° C. The mixture is then stirred into ice water, extracted with diethyl ether, and washed with sodium bicarbonate and water. After drying over magnesium sulfate, the mixture is concentrated under vacuum. The resultant crude product is chromatographed on silica gel with dichloromethane-acetone, yielding 1.1 g of 17α-(3-formyloxypropyl)-17β-hydroxy-4-androsten-3-one. $[α]_D^{22} = +68°$ (c=0.5 in chloroform).

EXAMPLE 21

2.0 g of 17β-hydroxy-17α-(3-hydroxypropyl)-4-androsten-3-one is dissolved in 10 ml of pyridine and stirred with 4 ml of acetic anhydride for one hour at room temperature. After precipitation in ice water, the thus-obtained precipitate is filtered off, washed with water, and taken up in dichloromethane. The solution is dried over magnesium sulfate and concentrated under vacuum. The resultant crude product is purified on silica gel with dichloromethane-acetone, thus obtaining 1.2 g of 17α-(3-acetoxypropyl)-17β-hydroxy-4-androsten-3-one. $[α]_D^{22} = +63°$ (c=0.5 in chloroform).

EXAMPLE 22

2.0 g of 17β-hydroxy-17α-(3-hydroxypropyl)-4-androsten-3-one is dissolved in 10 ml of pyridine and stirred with 4 ml of propionic acid anhydride for one hour at room temperature. Subsequently the mixture is diluted with water, extracted with diethyl ether, the combined ether phases are washed with water, dried over magnesium sulfate, and concentrated under vacuum. The thus-obtained crude product is chromatographed on silica gel with dichloromethane-acetone, yielding 1.4 g of 17β-hydroxy-17α-(3-propionyloxypropyl)-4-androsten-3-one. $[α]_D^{22} = +60°$ (c=0.5 in chloroform).

EXAMPLE 23

2.0 g of 17β-hydroxy-17α-(3-hydroxypropyl)-4-androsten-3-one is dissolved in 10 ml of pyridine and stirred with 4 ml of butyric anhydride for one hour at room temperature. Subsequently the mixture is diluted with water, extracted with diethyl ether, the combined ether phases are washed with water, dried over magnesium sulfate, and concentrated under vacuum. The resultant crude product is chromatographed on silica gel with dichloromethaneacetone, thus obtaining 1.2 g of 17α-(3-butyryloxypropyl)-17β-hydroxy-4-androsten-3-one. $[α]_D^{22} = +57°$ (c=0.5 in chloroform).

EXAMPLE 24

2.0 g of 17β-hydroxy-17α-(3-hydroxypropyl)-4-androsten-3-one is stirred in 10 ml of pyridine with 3 ml of pivalic anhydride and 300 mg of dimethylaminopyridine for 2 hours at room temperature, then diluted with water, extracted with diethyl ether, the combined organic phases washed with water, dried over magnesium sulfate, and concentrated under vacuum. The thus-obtained crude product is chromatographed on silica gel with dichloromethaneacetone, thus producing 1.3 g of 17β-hydroxy-17α-(3-trimethylacetoxypropyl)-4-androsten-3-one. $[α]_D^{22} = +51°$ (c=0.5 in chloroform).

EXAMPLE 25

A. 20 g of 17β-hydroxy-17α-(3-hydroxypropyl)-4-androsten-3-one is dissolved in 400 ml of methanol and 40 ml of dichloromethane and stirred at 0° C. with 40 ml of 2N sodium hydroxide solution and 50 ml of 30% strength hydrogen peroxide for 18 hours. The reaction mixture is stirred into ice water, the thus-separated precipitate is filtered off, washed with water, and taken up in dichloromethane. The solution is dried over magnesium sulfate and concentrated under vacuum. The resultant crude product is chromatographed on silica gel with dichloromethane-acetone, thus obtaining 14.6 g of 4β,5-epoxy-17β-hydroxy-17α-(3-hydroxypropyl)-5β-androstan-3-one.

B. Under the conditions described in Example 22, 14.6 g of 4β,5-epoxy-17β-hydroxy-17α-(3-hydroxypropyl)-5β-androstan-3-one yields 15.6 g of 4β,5-epoxy-17β-hydroxy-17α-(3-propionyloxypropyl)-5β-androstan-3-one.

C. A solution of 8.9 g of 4β,5-epoxy-17β-hydroxy-17α-(3-propionyloxypropyl)-5β-androstan-3-one in 175 ml of acetone is combined with 8.9 ml of concentrated hydrochloric acid and stirred for 6.5 hours at room temperature. Subsequently the mixture is poured into ice water, the precipitated solid matter is filtered off, washed with water, and taken up in dichloromethane. The solution is dried over magnesium sulfate and concentrated under vacuum. The resultant crude product is chromatographed on silica gel with dichloromethane-acetone, thus obtaining 4.9 g of 4-chloro-17β-hydroxy-17α-(3-propionyloxypropyl)-4-androsten-3-one. $[α]_D^{22} = +72°$ (c=0.5 in chloroform).

EXAMPLE 26

8.0 g of 4β,5-epoxy-17β-hydroxy-17α-(3-propionyloxypropyl)-5β-androstan-3-one is stirred in 320 ml of acetic acid and 8 ml of semiconcentrated sulfuric acid for 2 hours at 70° C. The largest portion of the acetic acid is distilled off, the residue is combined with dichloromethane, washed with dilute sodium hydroxide solution and water, dried over magnesium sulfate, and concentrated under vacuum. The thus-obtained crude product is chromatographed on silica gel with dichloromethaneacetone, thus yielding 5.2 g of 4,17β-dihydroxy-17α-(3-propionyloxypropyl)-4-androsten-3-one. $[α]_D^{22} = +21°$ (c=0.5 in chloroform).

EXAMPLE 27

A. Under the conditions described in Example 22, 9.84 g of 17β-hydroxy-17α-(3-hydroxypropyl)-4,6-androstadien-3-one yields 10.2 g of 17β-hydroxy-17α-(3-propionyloxypropyl)-4,6-androstadien-3-one.

B. 2.5 g of 17β-hydroxy-17α-(3-propionyloxypropyl)-4,6-androstadien-3-one is dissolved in 125 ml of benzene and refluxed for 6 hours with 2.5 g of dichlorodicyanobenzoquinone. After cooling, the mixture is filtered off from precipitated solid matter, the filtrate is washed with 1N sodium hydroxide solution and water, dried over magnesium sulfate, and concentrated under vacuum. The resultant crude product is chromatographed on silica gel with dichloromethane-acetone, yielding 1.2 g of 17β-hydroxy-17α-(3-propionyloxypropyl)-1,4,6-androstatrien-3-one. $[α]_D^{22} = -49°$ (c=0.5 in chloroform).

EXAMPLE 28

A. 22 g of 15β,16β-methylene-3β-(tetrahydropyran-2-yloxy)-5-androsten-17-one is dissolved in 400 ml of absolute tetrahydrofuran, and 65 g of potassium ethylate is added under ice cooling. Under agitation, a solution of 44 ml of propargyl alcohol in 88 ml of absolute tetrahydrofuran is added dropwise to this suspension. The reaction solution is stirred for 4 hours at room temperature, then stirred into 5 l of ice water, and neutralized with acetic acid. The precipitate is filtered off, washed, and dried. The resultant crude product is triturated with ethyl acetate, thus obtaining 23 g of 17α-(3-hydroxy-1-propynyl)-15β,16β-methylene-3β-(tetrahydropyran-2-yloxy)-5-androsten-17β-ol, mp 196° C.

B. A solution of 23 g of 17α-(3-hydroxy-1-propynyl)-15β,16β-methylene-3β-(tetrahydropyran-2-yloxy)-5-androsten-17β-ol in 1.3 l of methanol is combined with 3 spoonfuls of Raney nickel and hydrogenated until the hydrogen absorption ceases. Thereafter the mixture is vacuum-filtered from the catalyst, the solution is concentrated under vacuum, and the residue is recrystallized from ethyl acetate, yielding 14.1 g of 17α-(3-hydroxypropyl)-15β,16β-methylene-3β-(tetrahydropyran-2-yloxy)-5-androsten-17β-ol, mp 160° C.

C. Under the conditions described in Example 22, 14 g of 17α-(3-hydroxypropyl)-15β,16β-methylene-3β-(tetrahydropyran-2-yloxy)-5-androsten-17β-ol yields 13.2 g of 15β,16β-methylene-17α-(3-propionyloxypropyl)-3β-(tetrahydropyran-2-yloxy)-5-androsten-17β-ol.

D. 13 g of 15β,16β-methylene-17α-(3-propionyloxypropyl)-3β-(tetrahydropyran-2-yloxy)-5-androsten-17β-ol is stirred in 390 ml of methanol and 40 ml of water with 400 mg of pyridine tosylate for 3 hours at 50° C. Under vacuum, half of the solvent is removed by distillation, and the residue is precipitated into ice water. The resultant precipitate is taken up in dichloromethane and the solution is washed with sodium bicarbonate and water, dried over magnesium sulfate, and concentrated under vacuum. The thus-obtained crude product is chromatographed on silica gel with dichloromethane-acetone, yielding 8.2 g of 15β,16β-methylene-17α-(3-propionyloxypropyl)-5-androstene-3β,17β-diol.

E. A solution of 7.5 g of 15β,16β-methylene-17α-(3-propionyloxypropyl)-5-androstene-3β,17β-diol in 300 ml of toluene is combined with 15 ml of cyclohexanone and heated to boiling. After removing about 30 ml of toluene by distillation, 3 g of aluminum isopropylate is added and the mixture is distilled slowly for another 3 hours. Then the mixture is diluted with ethyl acetate, washed with 2N sulfuric acid and water, dried over magnesium sulfate, and concentrated under vacuum. The resultant crude product is chromatographed on silica gel with hexane-acetone, thus obtaining 5.1 g of 17β-hydroxy-15β,16β-methylene-17α-(3-propionyloxypropyl)-4-androsten-3-one. $[\alpha]_D^{22} = +41°$ (c=0.5 in chloroform).

EXAMPLE 29

A. Under the conditions described in Examples 1A-E and 2A-B, 17.5 g of 17β-hydroxy-18-methyl-4-androsten-3-one is converted into 4.2 g of 17β-hydroxy-18-methyl-17α-(3-propionyloxypropyl)-4-androsten-3-one.

B. 4.0 g of 17β-hydroxy-18-methyl-17α-(3-propionyloxypropyl)-4-androsten-3-one is refluxed in 200 ml of tert-butanol with 10 g of chloranil for 3 hours. The reaction solution is cooled, filtered, and concentrated under vacuum. The thus-obtained residue is dissolved in chloroform, and the solution is washed with water, 1N sodium hydroxide solution, and water, dried over magnesium sulfate, and concentrated under vacuum. The resultant crude product is chromatographed on silica gel with hexane-acetone, thus yielding 2.3 g of 17β-hydroxy-18-methyl-17α-(3-propionyloxypropyl)-4,6-androstadien-3-one, mp 169° C.

EXAMPLE 30

A. 1.5 g of freshly cut lithium pieces is added to 40 ml of absolute tetrahydrofuran and, under argon, 10 ml of 1-chloro-4-(1-ethoxyethoxy)butane is added thereto. The mixture is stirred for 5 minutes at room temperature and then cooled to 0° C. To this mixture is added 5 g of 3-methoxy-3,5-androstadien-17-one in 50 ml of tetrahydrofuran and stirred for 4 hours at 0° C. Thereafter the mixture is decanted off the unconsumed lithium and poured into saturated ammonium chloride solution. After extraction with dichloromethane, the organic phase is washed with water, dried over magnesium sulfate, and concentrated under vacuum. The thus-obtained crude product is chromatographed on silica gel with dichloromethane-acetone, yielding 1.42 g of 17β-hydroxy-17α-[4-(1-ethoxyethoxy)butyl]-4-androsten-3-one.

B. A solution of 1.4 g of 17β-hydroxy-17α-[4-(1-ethoxyethoxy)butyl]-4-androsten-3-one in 25 ml of methanol is combined with 2.5 ml of water and with 400 mg of oxalic acid, stirred for 3 hours at room temperature, and concentrated under vacuum. The residue is taken up in dichloromethane, the solution is washed with water, dried over magnesium sulfate, and concentrated under vacuum, thus obtaining 980 mg of 17β-hydroxy-17α-(4-hydroxybutyl)-4-androsten-3-one.

C. Under the conditions described in Example 22, 940 mg of 17β-hydroxy-17α-(4-hydroxybutyl)-4-androsten-3-one yields 750 mg of 17β-hydroxy-17α-(4-propionyloxybutyl)-4-androsten-3-one. $[\alpha]_D^{22} = +49°$ (c=0.5 in chloroform).

EXAMPLE 31

700 mg of 17β-hydroxy-17α-(3-hydroxypropyl)-1α-methyl-5α-androstan-3-one is allowed to stand at room temperature for 16 hours in 2.8 ml of pyridine and 0.7 ml of acetic anhydride. The mixture is worked up and chromatographed as described in Example 10E. The crude product is recrystallized from diisopropyl ether. Yield: 510 mg of 17α-(3-acetoxypropyl)-17β-hydroxy-1α-methyl-5α-androstan-3-one, mp 64° C.

EXAMPLE 32

A. A solution of 3.0 g of 3,3-ethylenedioxy-1α-methyl-5α-androstan-17-one in 30 ml of absolute tetrahydrofuran is combined in an ice bath under an argon stream with 9.0 g of potassium ethylate. Thereafter 4.5 ml of 3-butyn-1-ol, dissolved in 9 ml of absolute tetrahydrofuran, is added dropwise and the mixture stirred for 2.5 hours at room temperature. The reaction mixture is diluted with dichloromethane, the solution is washed with dilute sulfuric acid and water, dried, and evaporated. The residue is chromatographed on silica gel, thus obtaining 3.1 g of 3,3-ethylenedioxy-17α-(4-hydroxy-1-butynyl)-1α-methyl-5α-androsten-17β-ol as an oil.

B. 640 mg of 3,3-ethylenedioxy-17α-(4-hydroxy-1-butynyl)-1α-methyl-5α-androstan-17β-ol is allowed to stand in a mixture of 2.7 ml of pyridine and 0.64 ml of propionic anhydride for 17 hours at room temperature and then worked up as described in Example 10E. After chromatography on silica gel, 540 mg of 3,3-ethylenedioxy-1α-methyl-17α-(4-propionyloxy-1-butynyl)-5α-androstan-17β-ol is obtained as an oil.

C. 530 mg of 3,3-ethylenedioxy-1α-methyl-17α-(4-propionyloxy-1-butynyl)-5α-androstan-17β-ol is stirred in 5.3 ml of methanol with 0.53 ml of 8% sulfuric acid for 45 minutes at room temperature and then worked up as described in Example 10D. The residue is chromatographed on silica gel, thus obtaining 420 mg of 17β-hydroxy-1α-methyl-17α-(4-propionyloxy-1-butynyl)-5α-androstan-3-one, mp 120.5° C.

D. 400 mg of 17β-hydroxy-1α-methyl-17α-(4-propionyloxy-1-butynyl)-5α-androstan-3-one is hydrogenated under the conditions disclosed in Example 12A until two equivalents of hydrogen have been absorbed. The crude product is chromatographed on silica gel, thus obtaining 265 mg of 17β-hydroxy-1α-methyl-17α-(4-propionyloxybutyl)-5α-androstan-3-one as an oil.

EXAMPLE 33

A. 800 mg of 3,3-ethylenedioxy-17α-(4-hydroxy-1-butynyl)-1α-methyl-5α-androstan-17β-ol is hydrogenated in 24 ml of toluene and 16 ml of tetrahydrofuran with 240 mg of Lindlar catalyst as described in Example 11A, thus obtaining 800 mg of 3,3-ethylenedioxy-17α-(4-hydroxy-1-butenyl)-1α-methyl-5α-androstan-17β-ol.

B. A solution of 800 mg of 3,3-ethylenedioxy-17α-(4-hydroxy-1-butenyl)-1α-methyl-5α-androstan-17β-ol in 8 ml of methanol is combined with 0.8 ml of 8% strength sulfuric acid and stirred for 2 hours at room temperature. The reaction mixture is worked up as described in Example 10D and the residue is chromatographed on silica gel, thus obtaining 450 mg of 17β-hydroxy-17α-(4-hydroxy-1-butenyl)-1α-methyl-5α-androstan-3-one.

C. 440 mg of 17β-hydroxy-17α-(4-hydroxy-1-butenyl)-1α-methyl-5α-androstan-3-one is dissolved in 1.6 ml of pyridine, the solution is combined with 0.45 ml of propionic anhydride and allowed to stand at room temperature for 6 hours. Then the mixture is worked up as disclosed in Example 10E, yielding as the residue 520 mg of 17β-hydroxy-1α-methyl-17α-(4-propionyloxy-1-butenyl)-5α-androstan-3-one, mp 94° C.

EXAMPLE 34

A. 1.2 g of 3,3-ethylenedioxy-17α-(4-hydroxy-1-butynyl)-1α-methyl-5α-androstan-17β-ol is hydrogenated as described in Example 12A in 25 ml of 2-propanol and 20 ml of tetrahydrofuran with 1 g of Raney nickel catalyst. The crude product is chromatographed on silica gel, thus obtaining 710 mg of 3,3-ethylenedioxy-17α-(4-hydroxybutyl)-1α-methyl-5α-androstan-17β-ol.

B. 700 mg of 3,3-ethylenedioxy-17α-(4-hydroxybutyl)-1α-methyl-5α-androstan-17β-ol is allowed to stand in 7 ml of methanol with 0.7 ml of 8% strength sulfuric acid for 1.5 hours at room temperature and then worked up as described in Example 10D. Recrystallization from diisopropyl ether yields 390 mg of 17β-hydroxy-17α-(4-hydroxybutyl)-1α-methyl-5α-androstan-3-one, mp 129.5° C.

C. 350 mg of 17β-hydroxy-17α-(4-hydroxybutyl)-1α-methyl-5α-androstan-3-one is converted, under the conditions of Example 3, into 284 mg of oily 17α-(4-butyryloxybutyl)-17β-hydroxy-1α-methyl-5α-androstan-3-one.

EXAMPLE 35

A. A solution of 3.0 g of 3,3-ethylenedioxy-1α-methyl-5α-androstan-17-one in 30 ml of absolute tetrahydrofuran is combined with 9.0 g of potassium ethylate in an ice bath under argon. Then 4.5 ml of 4-pentyn-1-ol, dissolved in 9 ml of absolute tetrahydrofuran, is added dropwise thereto. The reaction mixture is stirred for 4 hours at room temperature and thereafter worked up as described in Example 32A. The residue is chromatographed on silica gel, thus obtaining 2.4 g of 3,3-ethylenedioxy-17α-(5-hydroxy-1-pentynyl)-1α-methyl-5α-androstan-17β-ol.

B. 2.3 g of 3,3-ethylenedioxy-17α-(5-hydroxy-1-pentynyl)-1α-methyl-5α-androstan-17β-ol is hydrogenated in a mixture of 24 ml of methanol and 24 ml of tetrahydrofuran with 240 mg of 10% palladium on calcium carbonate, as described in Example 12A. The crude product is chromatographed on silica gel. Yield: 2.2 g of 3,3-ethylenedioxy-17α-(5-hydroxypentyl)-1α-methyl-5α-androstan-17β-ol.

C. A solution of 2.2 g of 3,3-ethylenedioxy-17α-(5-hydroxypentyl)-1α-methyl-5α-androstan-17β-ol in 6.6 ml of pyridine and 2.2 ml of propionic anhydride is allowed to stand at room temperature for 16 hours and then worked up as described in Example 10E, thus obtaining 2.7 g of 3,3-ethylenedioxy-1α-methyl-17α-(5-propionyloxypentyl)-5α-androstan-17β-ol.

D. A solution of 2.7 g of 3,3-ethylenedioxy-1α-methyl-17α-(5-propionyloxypentyl)-5α-androstan-17β-ol in 27 ml of methanol is combined with 2.7 ml of 8% strength sulfuric acid and allowed to stand for one hour at room temperature. The reaction mixture is worked up as described in Example 10D, and the residue is chromatographed on silica gel. Yield: 590 mg of 17β-hydroxy-1α-methyl-17α-(5-propionyloxypentyl)-5α-androstan-3-one as an oil.

EXAMPLE 36

A. Under the conditions described in Example 21, 7.5 g of 4,5-epoxy-17β-hydroxy-17α-(3-hydroxypropyl)-androstan-3-one yields 7.2 g of 17α-(3-acetoxypropyl)-4,5-epoxy-17β-hydroxyandrostan-3-one.

B. Under the conditions disclosed in Example 26, 6.8 g of 17α-(3-acetoxypropyl)-4,5-epoxy-17β-hydroxyandrostan-3-one yields 3.6 g of 17α-(3-acetoxypropyl)-4,17β-dihydroxy-4-androsten-3-one.

EXAMPLE 37

3.24 g of 17β-hydroxy-17α-(3-hydroxypropyl)-4,6-androstadiene-3-one, under the conditions described in Example 23, yields 3.36 g of 17α-(3-butyryloxypropyl)-17β-hydroxy-4,6-androstadiene-3-one. UV:$\epsilon_{246}$=9600 (in methanol).

EXAMPLE 38

2.40 g of 17β-hydroxy-17α-(3-hydroxypropyl)-1-methyl-5-androst-1-ene-3-one is converted, under the conditions indicated in Example 2B, into 17β-hydroxy-1-methyl-17α-(propionyloxy)-5α-androst-1-ene-3-one. Yield: 1.21 g as an oil.

EXAMPLE 39

A. A solution of 14.0 g of 3,3-ethylenedioxy-1α-methyl-5-androstene-17-one in 140 ml of tetrahydrofuran is mixed, cooled to ice-cold temperature conditions, with 42 g of potassium methylate. Then 21 ml of 3-butin-1-ol is dissolved in 60 ml of tetrahydrofuran, added drop by drop within a period of 30 minutes, and the reaction mixture is then stirred for 4 hours at room temperature. The mixture is diluted with dichloromethane, washed with 0.4N of sulfuric acid and water, dried and concentrated in a vacuum. The residue is chromatographed using silica gel. 14.26 g of 3,3-ethylenedioxy-17α-(4-hydroxy-1-butinyl)-1α-methyl-5-androstene-17β-ol is obtained. A sample recrystallized from hexane acetic ester melts at 163° C.

B. 17.9 g of 3,3-ethylenedioxy-17α-(4-hydroxy-1-butinyl)-1α-methyl-5-androstene-17β-ol is hydrogenated in 90 ml of tetrahydrofuran and 145 ml of 2-propanol, with 840 mg of palladium/calcium carbonate catalyst (10% Pd) until two equivalent weights of hydrogen have been taken up. The product is filtered out of the catalyst and is then evaporated in a vacuum until dry. 17.4 g of 3,3-ethylenedioxy-17α-(4-hydroxybutyl)-1α-methyl-5-androstene-17β-ol is obtained in the form of a viscous oil.

C. 17.4 g of 3,3-ethylenedioxy-17α-(4-hydroxybutyl)-1α-methyl-5-androstene-17β-ol is heated for 2 hours in 250 ml of 90% acetic acid to a temperature of 60° C. The solution is evaporated in a vacuum and the residue is chromatographed using silica gel. Yield: 7.78 g of 17β-hydroxy-17α-(4-hydroxybutyl)-1α-methyl-4-androstene-3-one at a melting point of 202° C. (from dichloromethane-diisopropylether).

D. 2.0 g of 17β-hydroxy-17α-(4-hydroxybutyl)-1α-methyl-4-androstene-3-one is acetylated under the conditions of Example 21. The raw product is chromatographed using silica gel with hexane acetic ester. The yield obtained is 1.70 g of amorphous 17α-(4-acetoxybutyl)-17β-hydroxy-1α-methyl-4-androstene-3-one.

$[\alpha]_D^{22} = +67°$ (c=0.5 in chloroform).

UV: $\epsilon_{241} = 14,100$ (in methanol).

EXAMPLE 40

Under the conditions given in Example 2, 1.0 g of 17β-hydroxy-17α-(4-hydroxybutyl)-1α-methyl-4-androstene-3-one yields 997 mg of 17β-hydroxy-1α-methyl-17α-(4-propionyloxybutyl)-4-androstene-3-one.

$[\alpha]_D^{22} = +65°$ (c=0.5 in chloroform).

UV: $\epsilon_{242} = 14,600$ (in methanol).

EXAMPLE 41

Under the conditions given in Example 3, 2.0 g of 17β-hydroxy-17α-(4-hydroxybutyl)-1α-methyl-4-androstene-3-one yields 1.90 g of 17α-(4-butyryloxybutyl)-17β-hydroxy-1α-methyl-4-androstene-3-one.

$[\alpha]_D^{22} = +62°$ (=0.5 in chloroform).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An androstane of the formula

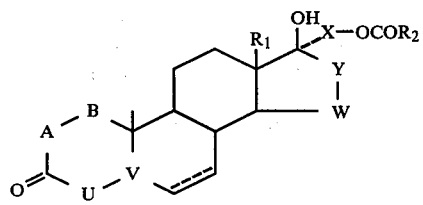

wherein

═ is a single bond or a double bond,
R₁ is methyl or ethyl,
R₂ is hydrogen or alkyl of 1–8 carbon atoms, —X— is —(CH₂)ₙ—, —CH═CH(CH₂)ₘ—, or —C≡C—(CH₂)ₘ— wherein n is an integer of 2 to 6 and m is an integer of 1 to 4,

—A—B— is —CH₂—CH₂—, —CH═CH—, —CCl═CH—,

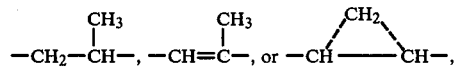

—U—V< is —CH₂—CH<, —C(OH)═C<, or —CCl═C<, and

—W—Y— is —CH₂—CH₂—, —CH₂—C(CH₃)₂—, or

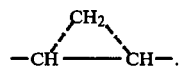

2. An androstane of claim 1 of the formula

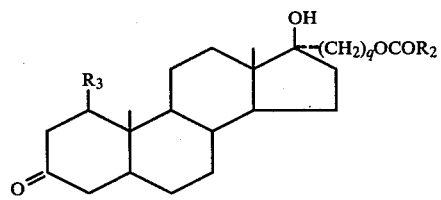

wherein

R₂ is as defined in claim 1,
q is 3 or 4, and
R₃ is hydrogen or methyl.

3. 17α-(3-Acetoxypropyl)-17β-hydroxy-5α-androstan-3-one, a compound of claim 1.

4. 17β-Hydroxy-17α-(3-propionyloxypropyl)-5α-androstan-3-one, a compound of claim 1.

5. 17α-(3-Butyryloxypropyl)-17β-hydroxy-5α-androstan-3-one, a compound of claim 1.

6. 17α-(3-Butyryloxy-1-propynyl)-17β-hydroxy-5α-androstan-3-one, a compound of claim 1.

7. 17α-(3-Butyryloxy-1-propenyl)-17β-hydroxy-5α-androstan-3-one, a compound of claim 1.

8. 17β-Hydroxy-17α-(3-propionyloxy-1-propynyl)-5α-androstan-3-one, a compound of claim 1.

9. 17α-(3-Butyryloxypropyl)-1-methyl-5α-androst-1-en-3-one, a compound of claim 1.

10. 17β-Hydroxy-1α-methyl-17α-(3-propionyloxy-1-propynyl)-5α-androstan-3-one, a compound of claim 1.

11. 17β-Hydroxy-1α-methyl-17α-(3-propionyloxypropyl)-5α-androstan-3-one, a compound of claim 1.

12. 17β-Hydroxy-1α-methyl-17α-(3-propionyloxy-1-propynyl)-5α-androstan-3-one, a compound of claim 1.

13. 17α-(3-Butyryloxypropyl)-17β-hydroxy-1α-methyl-5α-androstan-3-one, a compound of claim 1.

14. 17α-(3-Hexanoyloxypropyl)-17β-hydroxy-1α-methyl-5α-androstan-3-one, a compound of claim 1.

15. 17β-Hydroxy-1α-methyl-17α-(2-propionyloxyethyl)-5α-androstan-3-one, a compound of claim 1.

16. 17β-Hydroxy-1α-methyl-17α-(4-propionyloxybutyl)-5α-androstan-3-one, a compound of claim 1.

17. 17β-Hydroxy-1α,16α,16β-trimethyl-17α-(3-propionyloxypropyl)-5α-androstan-3-one, a compound of claim 1.

18. 17β-Hydroxy-1α,2α-methylene-17α-(3-propionyloxypropyl)-5α-androstan-3-one, a compound of claim 1.

19. 2-Chloro-17β-hydroxy-17α-(3-propionyloxypropyl)-5α-androst-1-en-3-one, a compound of claim 1.

20. 17α-(3-Formyloxypropyl)-17β-hydroxy-4-androsten-3-one, a compound of claim 1.

21. 4-Chloro-17β-hydroxy-17α-(3-propionyloxypropyl)-4-androsten-3-one, a compound of claim 1.

22. 4,17β-Dihydroxy-17α-(3-propionyloxypropyl)-4-androsten-3-one, a compound of claim 1.

23. An androstane of the formula

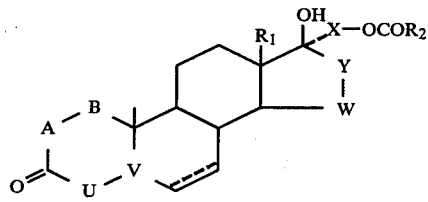

wherein
══is a single bond or a double bond,
$R_1$ is methyl or ethyl,
$R_2$ is hydrogen or alkyl of 1-8 carbon atoms,
—X— is —$(CH_2)_n$—, —CH=CH$(CH_2)_m$—, or —C≡C—$(CH_2)_m$—
wherein n is an integer of 2 to 6 and m is an integer of 1 to 4,
—A—B— is —CH=CH—, —CCl=CH—,

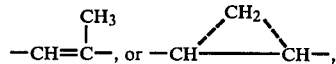

—U—V< is —$CH_2$—CH<, —CH=C<, —C(OH)=C<, or —CCl=C<, and
—W—Y— is —$CH_2$—$CH_2$—, —$CH_2$—$C(CH_3)_2$—, or

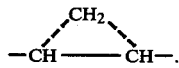

24. 17β-Hydroxy-17α-(3-propionyloxypropyl)-1,4,6-androstatrien-3-one, a compound of claim 23.

25. 17α-(3-Acetoxypropyl)-17β-hydroxy-1α-methyl-5α-androstan-3-one, a compound of claim 1.

26. 17β-Hydroxy-17α-(4-propionyloxy-1-butynyl)-1α-methyl-5α-androstan-3-one, a compound of claim 1.

27. 17β-Hydroxy-1α-methyl-17α-(4-propionyloxy-1-butenyl)-5α-androstan-3-one, a compound of claim 1.

28. 17α-(4-Butyryloxybutyl)-17β-hydroxy-1α-methyl-5α-androstan-3-one, a compound of claim 1.

29. 17β-Hydroxy-1α-methyl-17α-(5-propionyloxypentyl)-5α-androstan-3-one, a compound of claim 1.

30. 17α-(3-Acetoxypropyl)-4,17β-dihydroxy-4-androsten-3-one, a compound of claim 1.

31. A compound of claim 23 wherein $R_2$ is alkyl of 1-3 carbon atoms.

32. A compound of claim 23 wherein in X, n is 2-4 or m is 1 or 2.

33. A pharmaceutical composition of claim 23 comprising one or two of said effective compounds.

34. A pharmaceutical composition of claim 23 wherein the amount of effective compound is 0.05–5.0% by weight.

35. A method of suppressing sebum in a patient in need of such treatment comprising topically administering to the patient an amount of a pharmaceutical composition effective to suppress sebum and which comprises a pharmaceutically acceptable carrier and an effective amount of a compound of the formula

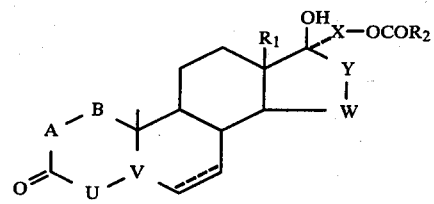

wherein
══is a single bond or a double bond,
$R_1$ is methyl or ethyl,
$R_2$ is hydrogen or alkyl of 1-8 carbon atoms,
—X— is —$(CH_2)_n$—, —CH=CH$(CH_2)_m$—, or —C≡C—$(CH_2)_m$—
wherein n is an integer of 2 to 6 and m is an integer of 1 to 4,
—A—B— is —$CH_2$—$CH_2$—, —CH=CH—, —CCl=CH—,

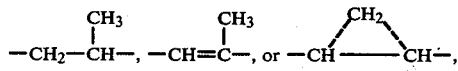

—U—V< is —$CH_2$—CH<, —CH=C<, —C(OH)=C<, or —CCl=C<, and
—W—Y— is —$CH_2$—$CH_2$—, —$CH_2$—$C(CH_3)_2$—, or

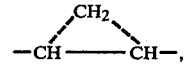

with the proviso that when —A—B— is —$CH_2$—$CH_2$—, and —U—V— is —CH=C<, and ══ is a double bond, and $R_1$ is $CH_3$, and —W—Y— is —$CH_2$—$CH_2$—, and X is —$(CH_2)_3$—, then $R_2$ is not —$CH_3$.

36. A method of suppressing sebum in a patient in need of such treatment comprising topically administering to the patient an amount of a pharmaceutical composition effective to suppress sebum and which comprises a pharmaceutically acceptable carrier and an effective amount of 17α-(3-acetoxypropyl)-17β-hydroxy-4,6-androstadien-3-one.

37. A topically administrable pharmaceutical composition comprising an amount of a compound of claim 23 effective to suppress sebum and a pharmaceutically acceptable carrier.

38. A topically administrable pharmaceutical composition comprising an amount of a compound of claim 1 effective to suppress sebum and a pharmaceutically acceptable carrier.

39. A method of suppressing sebum in a patient in need of such treatment comprising topically administering to the patient an amount of a pharmaceutical composition of claim 23 effective to suppress sebum.

40. A method of suppressing sebum in a patient in need of such treatment comprising topically administering to the patient an amount of a pharmaceutical composition of claim 1 effective to suppress sebum.

41. A compound of claim 1 wherein $R_2$ is alkyl of 1–3 carbon atoms.

42. A compound of claim 1 wherein in X, n is 2–4 or m is 1 or 2.

43. A pharmaceutical composition of claim 1 comprising one or two of said effective compounds.

44. A pharmaceutical composition of claim 1 wherein the amount of effective compound is 0.05–5.0% by weight.

* * * * *